United States Patent [19]

Gangemi

[11] 4,077,882

[45] Mar. 7, 1978

[54] ISOLATING AND BLOOD PRESSURE TRANSMITTING APPARATUS FOR EXTRACORPOREAL BLOOD TREATMENT SYSTEM

[76] Inventor: Ronald Gangemi, 17752 Amberton La., Huntington Beach, Calif. 92646

[21] Appl. No.: 726,807

[22] Filed: Sep. 27, 1976

[51] Int. Cl.$^2$ ............................................. B01D 31/00
[52] U.S. Cl. ........................................ 210/90; 210/94; 210/321 B
[58] Field of Search .............. 73/406, 410; 128/214 E; 210/90, 94, 321 B; 92/5 R; 138/30; 23/258.5 M

[56] References Cited

U.S. PATENT DOCUMENTS

| 2,689,481 | 9/1954 | Qulat | 73/410 X |
| 3,713,341 | 1/1973 | Madsen et al. | 73/406 |
| 3,780,693 | 12/1973 | Parr | 73/410 X |
| 3,908,653 | 9/1975 | Kettering | 210/90 X |
| 3,958,558 | 5/1976 | Dunphy et al. | 73/410 X |

*Primary Examiner*—Frank A. Spear, Jr.
*Attorney, Agent, or Firm*—Gary Appel

[57] ABSTRACT

An isolating and blood pressure transmitting apparatus for use in an extracorporeal blood treatment system or the like comprises a generally cylindrical, transparent plastic chamber with a housing having axially opposing inlet and outlet portions. The inlet portion is connected to a blood pumping and purifying portion of the system for receiving pressurized blood therefrom; the outlet portion is connected to a conventional pressure transducer which, in response to blood pressure transmitted thereto, controls blood pumping valving to maintain blood pressure in the system within predetermined limits. The chamber housing has a diameter and an axial length substantially greater than the diameter of the inlet and outlet portions, the chamber having an appreciable volume to absorb pressure surges. A thin flexible membrane, formed in a frustoconical shape is disposed across the housing to physically isolate the pressure transducer from the blood pumping and purifying portion of the system. A plurality of annular membrane wall segments, interconnected into a staircase-like structure, form the conical portion of the membrane and permit such portion to axially expand and contract or telescope in response to blood pressure variations at the inlet portion, pressure being thereby transmitted to the transducer through a pressure transmitting media. In extreme variations of blood pressure the conical membrane can turn inside out and sweep out major portions of the chamber volume, enabling use of the apparatus with very sensitive transducers. Axial portions of the conical membrane portion may be formed having an appearance contrasting with adjacent axial portions to enhance visual monitoring of membrane expansion and hence of blood pressure in the system. The membrane steps may be formed of varying thickness to provide non-linear expansion and contraction of the conical membrane portion in response to linear blood pressure variations at the inlet portion and to provide pressure surge protection for the transducer.

12 Claims, 7 Drawing Figures

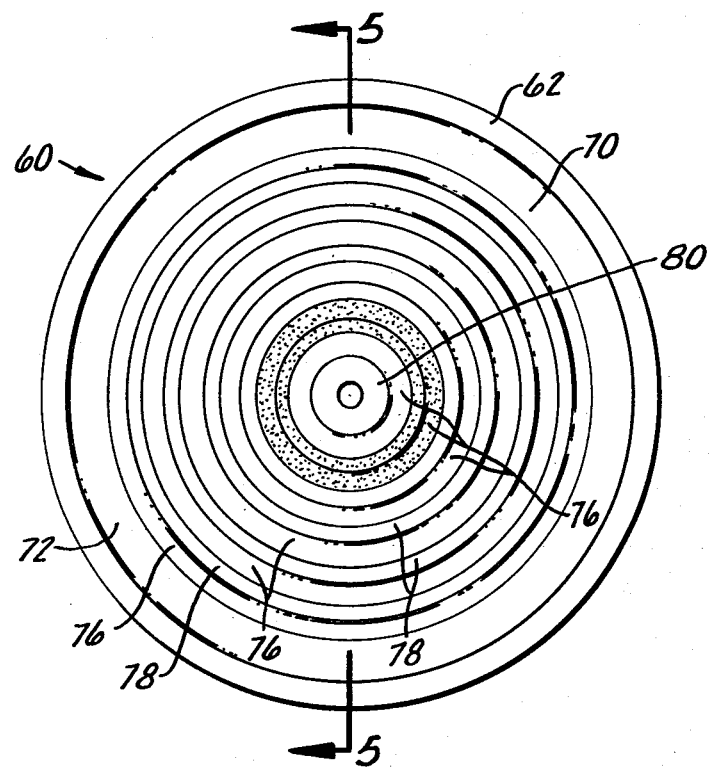
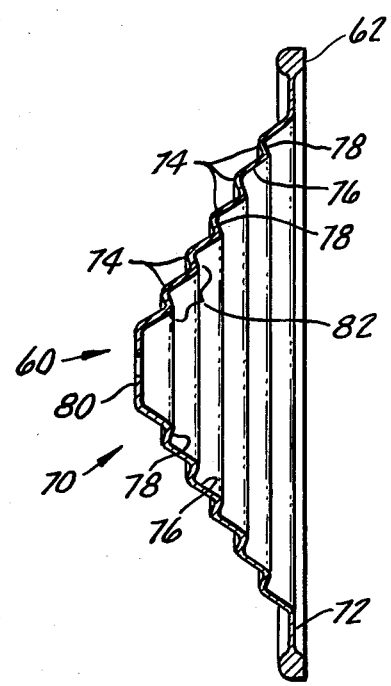
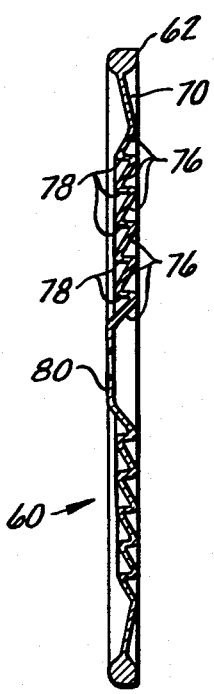
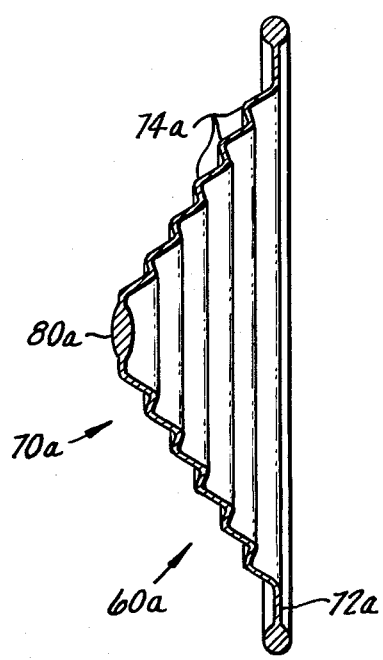

ISOLATING AND BLOOD PRESSURE TRANSMITTING APPARATUS FOR EXTRACORPOREAL BLOOD TREATMENT SYSTEM

BACKGROUND OF THE INVENTION

1. Field of the Invention

The present invention relates generally to the field of extracorporeal blood treatment systems, and more specifically to those portions of such systems relating to pressure sensing and pressure surge protection.

2. Description of the Prior Art

Various types of extra-corporeal blood treatment systems for humans, or external artificial kidneys, are, and have for some time, been available for removing waste products and impurities from the blood of patients having diseased, damaged, or impaired kidneys.

In order to perform this life saving function in a satisfactory manner, the systems must be provided with delicate system pressure sensing elements or transducers and associated electric or pneumatic controls for the system blood pump and valves. These transducers sense variations in system blood pressure as blood is pumped through the cleansing apparatus and, in response thereto, regulate the pump and valves to prevent high or low pressures which might cause damage to the patients' internal blood circulating system or delicate internal organs.

However, when these transducers are connected directly to the blood treatment part of the system, sharp high pressure transients, caused, for example, by equipment malfunction, may damage the transducers to the extent that they cannot later accurately sense, and hence control, system pressure. This may occur even if the pressure transient were such that the patient undergoing treatment was not injured. And even if a patient were injured, it might not be readily apparent that the transducer (or transducers) was damaged, and hence control of system pressure for future patients could be impaired.

In addition, if the transducer is directly coupled to the blood treatment portion of the system, it may be a source of contamination to the blood being treated. Even though the various blood lines and purifying apparatus may be replaced or sterilized after each use, the transducer, which is a relatively permanent part of the system, may be contaminated and introduce particles of a previous patients blood into a next patients blood. Or, if the transducer is damaged by pressure transients, it may become a source of other types of contaminants, such as metal particles, air, or oil.

Even if the transducer is not damaged by sharp blood pressure transients it may not be sufficiently responsive to control the system pressure within a pressure range not injurious to the patient.

As a result of these and other problems, the pressure transducer should be effectively isolated from blood being pumped through the system and means should be provided to absorb pressure transients both to protect patients and the transducer from injury. Although in some instances diaphragm type apparatus have been employed to isolate the pressure transducers from other portions of the blood treatment apparatus through which flows a patient's blood, such diaphragms, whose action depends upon stretching, are generally unsatisfactory because they prove to eventually crack in use and have not sufficient membrane memory to return to their original state, nor do they provide a means of warning if the isolator is over pressurized, absorb air or other contaminants from the sensor portion into the blood being treated, and also because the response of the diaphragm to pressure fluctuations in the blood treatment portion is always relatively constant and cannot readily be made to vary in a predetermined manner, as may be desirable in some applications.

SUMMARY OF THE INVENTION

In combination with an extracorporeal blood treatment system or the like having a blood pumping and purifying portion for connecting to a patient, at least one pressure sensing transducer for sensing pressure in the pumping and purifying portion and control means responsive to the transducer for controlling blood pressure in the pumping and purifying portion within predetermined limits, apparatus for isolating the transducer from the pumping and purifying portion while transmitting pressure of the blood therein to the transducer, the apparatus comprising a pressure chamber including a housing with axially apposing inlet and outlet portions, means for connecting the inlet portion to the system pumping and purifying portion and the outlet portion to the transducer and membrane means disposed across the housing to physically isolate the inlet and outlet portions and preventing flow of blood therebetween.

The membrane means includes a flexible, gas and liquid impermeable membrane formed in a frustoconical shape from a plurality of annular wall segments interconnected into a staircase-like structure which axially expands in either axial direction and contracts or telescopes within the housing in response to blood pressure variations at the inlet portion, and thereby transmits system blood pressure, through a pressure transmitting media to the transducer.

More particularly, the membrane wall segments are formed of a uniform thickness, thereby enabling generally linear expansion and contraction of conical portions of the membrane. The housing may be formed of substantially transparent material enabling an observer to visually monitor expansion and contraction of the membrane and hence visually monitor blood pressures in the pumping and purifying portion of the system. Observation of membrane movement may be enhanced by constructing first portions of the membrane conical portion to have a contracting appearance relative to axially adjacent portions of the membrane. The contracting construction may be such that upon expansion the contracting portion first becomes visible at a preselected pressure.

The annular wall segments may be constructed to be of varying thickness, the segments closest to an outer edge of the membrane being thinner than those further from the outer edge. When contracted in this manner, the membrane axially expands and contracts in a non-linear manner. This enables pressure surge protection of the transducer.

Since the membrane, upon expansion and contraction, unfolds and folds rather than stretching like a conventional diaphragm, there is a reduced tendency for the membrane to crack or break in use. Also, this method of construction, in conjunction with a relatively large diameter, and axially long chamber, permits the membrane to sweep out large volumes of the chamber as it expands and contracts in response to system blood pressure variations and fluctuations, rather than small volumes as would a diaphragm. This adapts the apparatus for use with very sensitive transducers.

Thus the apparatus performs the several important functions of physically separating the transducer from the blood pumping and purifying portion of the system to prevent contamination of the blood in the system, of transmitting system blood pressure in a linear or non-linear manner, according to the type of membrane used, and protecting the transducer from possibly damaging blood pressure spikes.

The apparatus is constructed in a relatively inexpensive manner so that it can be disposed of after a single use, if desired.

BRIEF DESCRIPTION OF THE DRAWINGS

A better understanding of the present invention may be had from a consideration of the following detailed description, taken in conjunction with the accompanying drawings in which:

FIG. 4 is an end elevational view along line 4—4 of FIG. 2, showing, in an expanded configuration, a blood isolating and pressure transfering membrane used in the apparatus, FIG. 5 is a cross sectional view along line 5—5 of FIG. 4, showing construction of the membrane;

FIG. 6 is a cross sectional view of the membrane of FIGS. 4 and 5, showing the membrane in a collapsed or telescoped configuration; and FIG. 7 is a cross sectional view of a variation of the membrane of FIG. 4-6, showing features of its construction.

DESCRIPTION OF THE PREFERRED EMBODIMENT

Figure 1:
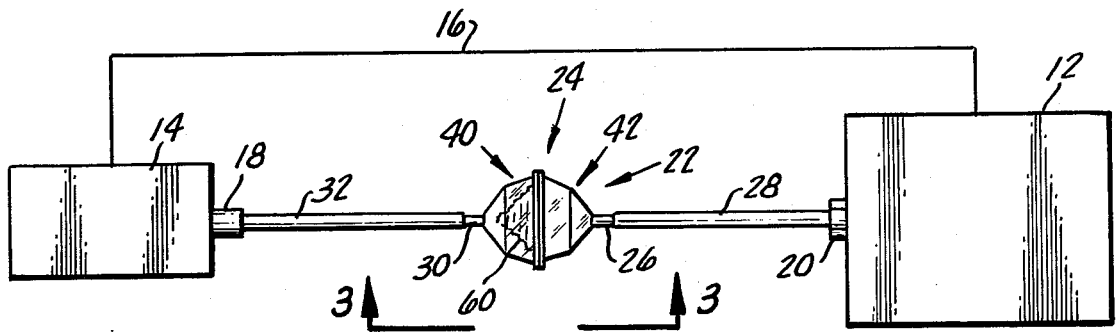
FIG. 1 is a drawing, partially in block diagram form, of an extracorporeal blood treatment system using a blood isolating and pressure transfering apparatus.

An extracorporeal blood treatment system for example, a kidney dialysis machine or the like 10, as seen in FIG. 1, includes a blood pumping and purifying portion 12 adapted for connecting to the blood stream of a patient (not shown) for cleansing the patient's blood and a control portion 14, connected to the pumping and purifying portion by connecting means 16 for pressure control of the system in a conventional manner. The control portion 14 includes at least one very sensitive pressure sensing transducer 18, of conventional design, which has electrical outputs proportional to the pressure sensed. By means of these proportional electrical outputs, blood pressure in the pumping and purifying portion is controlled within preestablished limits.

Connected between the transducers 18 and a portion 20 of the pumping and purifying portion 12 through which flows, or which receives, pressurized blood, in a blood isolation and pressure transfering means 22. Such means 22 functions to transfer or transmit pressure of blood in the pumping and purifying portion 12 to the pressure transducer 18, which in turn, through the control portion 14, controls blood pumping and valving in the portion 12. At the same time, the means 22 isolates blood in the pumping and purifying portion 12 from air or other contaminants which may be associated with the transducer 18. Additionally, the means 22 functions as a small pressure surge chamber which dampens out pressure spikes in the portion 12 and protects the transducer 18 from pressure surges.

Included in the means 22 is an isolation and pressure transfering or pressure chamber 24 which has an inlet portion 26, connected by a blood line 28 to the portion 20, and an outlet portion 30, connected by a pressure tube 32 to the transducer 18. (See also FIG. 2). The blood line 28 and tube 32 comprise conventional non-toxic medical grade plastic tubing of a type commonly employed in extracorporeal blood treatment systems. The portions 26 and 30 are on the longitudinal axis of the chamber 24 in an apposing relationship.

Figure 2:
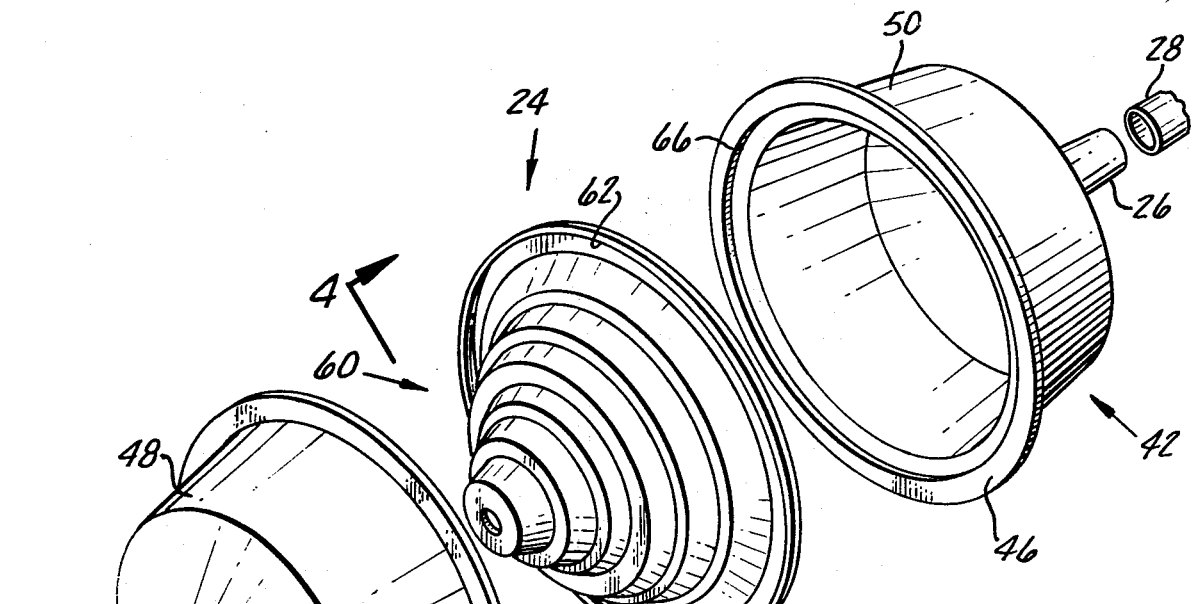
FIG. 2 is an exploded perspective drawing of the blood isolating and pressure transfering apparatus, showing elements thereof.
Figure 3:
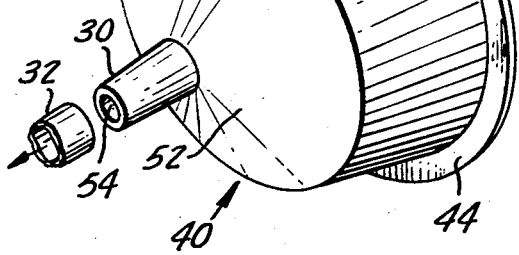
FIG. 3 is a side elevational view, partially cut away, along line 3—3 of FIG. 1, showing features of the blood isolating and pressure transfering apparatus.
Figure 3:
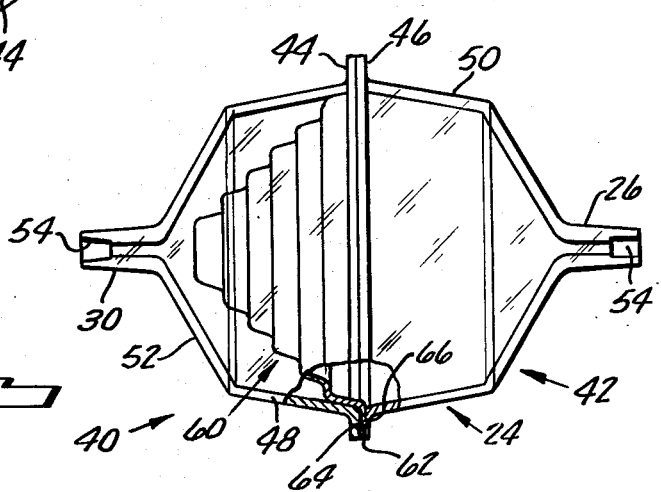

As best seen in FIGS. 2 and 3, the chamber 24 includes a rigid, generally transparent medical grade plastic housing formed of a first axial housing segment 40 and a second axial housing segment 42, the inlet portion 26 forming an inlet to the second segment and the outlet portion 30 forming an outlet to the first segment. Preferably the two housing segments 40 and 42 are substantially identical, having outwardly projecting mating central flanges 44 and 46 respectively, slightly converging circular wall portions 48 and 50, connected to the flanges 44 and 46 respectively, and relatively steeply converging, generally conical ends 50 and 52 respectively.

As seen in FIG. 3, outer circular surfaces the inlet and outlet portions 26 and 30 are slightly converging towards exposed entrances and exit ends, respectively, enabling tubing to be tightly slipped thereover. However, each such such portion 26 and 30 is also formed having an enlarged cylindrical bore 54 at the exposed ends enabling ends of tubing to be received therein. That is, the portions 26 and 30 have combined male and female tubing receiving characteristics.

The housing, comprising segments 40 and 42 is, when assembled, impervious to gas or liquids, is non-porous and easy to clean and is resistant to shock and pressure changes therein. Generally cylindrical in shape, the housing, and hence the chamber 24, has a transverse cross sectional diameter at any axial point substantially greater than that of the inlet and outlet portions 26 and 30, and likewise has an axial length, exclusive of such portions 26 and 30, substantially greater than the diameters of these portions. Thus, there is substantial volume in the chamber 24, thereby making it suitable for functioning as a surge chamber.

Installed within the chamber 24, between the housing segment flanges 44 and 46, is a strong thin, flexible blood isolating and pressure transmitting membrane 60. The outer circular periphery of the membrane 60 is formed with a siding bead 62 (FIGS. 3-5) which, upon assembly is received, in sealing relationship, into mating annular recesses 64 and 66 formed in abutting faces of the housing segment flanges 44 and 46 respectively (FIG. 3).

As best seen in FIGS. 4 and 5, the membrane 60 is constructed having a hollow, generally frustoconical shape, a conical portion 70 thereof being formed continuously with a circular flange portion 72, the latter of which includes the bead 62. The conical portion 70 is formed in a general stair-case or accordian-pleated manner comprising a plurality (six being shown) of interconnected steps 74, each of which is formed of annular wall segments, a first, generally axial portion 76 of each segment being directed in a converging direction towards the closed end of the conical portion 70 and a second generally radial portion 78 being directed generally orthogonally to the first portion 76. The closed end of the cone portion 70, terminates in a flat small diameter, transverse end segment 80.

The staircase-type construction of the membrane 60 permits the conical portion 70 to axially expand to the extended or nearly extended configuration of FIG. 5 and to axially contract or telescope into an intermediate, generally folded configuration shown in FIG. 6 without any significant stretching. Such construction also enables the conical portion 70 to turn inside out in response to a change from positive to negative blood pressure at the housing inlet portion 26. That is, the conical portion 70 can axially contract or telescope in a uniform manner from the positive inlet pressure configuration illustrated in FIGS. 3 and 5, to the intermediate configuration of FIG. 6 as pressure in the inlet portion 26 is reduced. As pressure in the inlet portion 26 further decreases to a negative value, the conical portion 70 then axially extends the expands towards the inlet portion. Relatively uniform contraction and expansion of the cone portion 70 is permitted by the staircase-type construction, and the degree of extension/contraction is a direct function of blood pressure at the housing inlet portion. The housing segment 44 to the transducer side of the membrane 60, as well as the tube 32 leading to the transducer 18 are filled with a pressure transmitting media, such as air or gaseous nitrogen. Axial movement of the membrane conical portion 70, in response to blood pressure fluctuations in the inlet portion 26, transmits the blood pressure to the transducer 18 through the pressure transmitting media. It is emphasized that the conical portion 70 of the membrane 60, because of its manner of construction, is permitted to move axially to sweep out a large volume of the chamber 24 thereby making it particularly adapted for use with very sensitive transducers.

A gas and liquid seal is provided between the housing segments 40 and 42, and hence between the transducer 18 and the pumping and purifying portion 12 of the system 10, by the membrane 60. Because movement of the membrane conical portion 70 is by means of axial unfolding and folding, rather than by stretching, the membrane 60 is generally more resistant to cracking or breaking than a conventional diaphragm which must stretch to operate. The membrane 60 may, for example, be constructed of a thin film, approximately 0.020 inches thick of a strong, flexible silicone rubber material such as Dow Corning.

Because axial extending and contracting of the membrane conical portion 70 is relatively uniformly related to the blood pressure at the housing inlet portion 26, the extent of extension and contraction, as well as the direction of extension — away from or towards the housing inlet portion — as can be seen through the transparent housing segments 40 and 44, provides an operator with a visible indicator of blood pressure in the pumping and purifying portion 12. A visual monitoring of the proper blood pressure in the system 10 is thereby provided which is in addition to any indicators which may be associated with the transducer 18. Since the membrane 60 is directly operated by blood pressure in the system, such a visual indication of system blood pressure serves as an important check of, or back-up for, the system control portion 14.

To enhance this visual monitoring of blood pressure by observing the degree and direction of extension of the conical portion 70, selected ones, for example step 82, of the steps 74 may be formed having an appearance which contrasts with that of adjacent steps. For example, the selected steps 82 may be of a contrasting color. When the conical portion 70 is in the intermediate configuration of FIG. 6 and even as some axial extension occurs, the selected step 82 remains hidden in the folds. As more pressure in the inlet portion 26 causes greater extension of the membrane conical portion 70, the contrast of the selected step 82 becomes visible. In this manner, the membrane 60 can be constructed so that when a preselected, for example, a near maximum allowable, blood pressure in the system is reached, the contrasting selected step 82 becomes visible.

By constructing the membrane 60 of a material of uniform thickness (except for the bead 62) the degree of axial expansion/contraction of the conical portion 70 is directly related, in a generally proportional manner, to the blood pressure at the housing inlet portion 26. Thus, if the axial expansion doubles, as an illustration, the blood pressure will also have had to about double.

However, by constructing various portions of the membrane of different thicknesses, the generally directly proportional expansion can be caused to be changed. It can be changed so that, for example, a doubling of blood pressure at the inlet portion 26 will cause either more or less than a doubling of extension of the conical portion 70. As an illustration, with no limitation intended or implied, the wall thickness of a conical portion 70a of a variation membrane 60a can be constructed to vary in a generally uniform manner, as seen in FIG. 7, from a flange 72a to a transverse end segment 80a, steps 74a closest to the flange being for example, thinner than steps closest to the end portion. The conical portion wall thickness may, in this manner, vary from about 0.012 inches to 0.020 inches. Since those of the steps 74a closest to the flange 72a are thinner and hence more flexible than other steps closer to the end segment 80a, axial extension and telescoping or contraction in response to blood pressure at the inlet portion 26 will start at the steps near the flange. This characteristic, in combination with forming selected ones of the steps 74a to be of visually contrasting appearance, enhances the visual observation of preselected pressures, as described above.

The variable thickness of the membrane 60a also enables the membrane to function as a dampening device, as well as a gas and liquid barrier and a pressure transmitter, to protect a sensitive transducer from otherwise damaging high blood pressure spikes.

As an illustrative example, the chamber 24 may be about 1½ inches in diameter and vary in axial length from about 2 to 2½ inches, having a corresponding volume of from about 7-15 cc's and being adapted for maximum pressures of about 600 mm/mercury.

The chamber 24 is constructed in a comparatively inexpensive manner to be disposable, if desired, after a single use.

Although there has been described above specific arrangements of a blood isolating and pressure transferring apparatus for use in extracorporeal blood treatment systems and a variation thereof, in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the appended claims.

What is claimed is:

1. In combination with an extracorporeal blood treatment system having a blood pumping and purification portion for connecting to a patient, at least one pressure sensing transducer for sensing pressure in the pumping and purifying portion and control means responsive to the pressure transducer for controlling blood pressure in the pumping and purifying portion within predetermined limits, apparatus for isolating the transducer from blood flowing in the pumping and purifying portion while permitting the pressure of the blood therein to be transmitted to the transducer, the apparatus comprising:
 (a) a substantially rigid pressure chamber including a gas and liquid impermeable, non-toxic housing having relatively apposing, axial pressure inlet and outlet portions
  said housing having a transverse cross sectional area substantially greater than transverse cross sectional areas of the inlet and outlet portions,
 (b) means for connecting the inlet portion to a blood carrying portion of the pumping and purifying portion for receiving pressurized blood therefrom and for connecting the outlet portion to the transducer for transmitting pressure of the pressurized blood thereto, and
 (c) membrane means disposed transversely across the pressure chamber for physically isolating the outlet portion from the inlet portion and preventing the flow of pressurized blood therebetween
  said membrane means comprising a flexible gas and fluid impermeable membrane formed into a generally frustoconical configuration and having outer peripheral edge portions connected to walls of the housing
  said membrane being formed having a plurality of concentric, annular wall segments interconnected to form a collapsible staircase-like structure permitting the membrane to be extended in either axial direction and being turned inside out as it passes through a central position between extension in opposite directions in response to positive and negative pressures transmitted to an inlet portion side thereof by the pressurized blood, the membrane thereby causing pressure of the pressurized blood to be transmitted to the transducer through the outlet portion and a preselected pressure transmitting media contained between an outlet side of the membrane and the transducer.

2. The apparatus according to claim 1, wherein said annular wall segments are formed having a substantially uniform thickness.

3. The apparatus according to claim 1, wherein said annular wall segments are formed having substantially uniformly varying thickness, the wall segments closest to the outer periphery being substantially thinner than the wall segments most remote from the outer periphery.

4. The apparatus according to claim 3, wherein the wall segment thickness varies from about 0.012 inches adjacent to the outer periphery to about 0.020 inches for wall segments most remote from the outer periphery.

5. The apparatus according to claim 1, wherein the membrane is formed having about six steps, each step being of substantially the same size.

6. The apparatus according to claim 1, wherein the housing is formed of substantially transparent material to thereby permit visual observation of the membrane.

7. The apparatus according to claim 6, wherein first selected portions of the membrane are formed to be color contrasting to axially adjacent second portions of the membrane, axial expansion and telescoping of the membrane causing, respectively, the first portion to be visible and non-visible, a visual indication of a preselected blood pressure being provided when the first portion is visible.

8. The apparatus according to claim 1, wherein the housing is formed having an axial length substantially greater than transverse cross sectional dimensions of the inlet and outlet portions, the chamber thereby having a relatively substantial volume.

9. The apparatus according to claim 8, wherein the membrane is generally axially centered in the chamber and wherein the membrane is operative for sweeping out substantially the entire volume of the chamber in response to extreme ranges of pressure in the blood pumping and purifying portion.

10. The apparatus according to claim 1, wherein the housing is generally cylindrical in shape, the outer periphery of the membrane being substantially circular.

11. The apparatus to claim 9, wherein the inlet and outlet portions are generally conical in shape, converging, respectively, towards the pumping and purifying portion and the transducer.

12. The apparatus according to claim 1, wherein the membrane is formed of a silicon rubber material having a substantially uniform thickness of about 0.020 inches.

* * * * *